(12) United States Patent
Wüst et al.

(10) Patent No.: US 9,470,245 B2
(45) Date of Patent: Oct. 18, 2016

(54) DEVICE AND METHOD FOR GENERATING VACUUM FOR VACUUM CEMENTING SYSTEMS

(71) Applicant: HERAEUS MEDICAL GMBH, Wehrheim (DE)

(72) Inventors: Edgar Wüst, Gross-Umstadt (DE); Sebastian Vogt, Erfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 501 days.

(21) Appl. No.: 13/667,144

(22) Filed: Nov. 2, 2012

(65) Prior Publication Data
US 2013/0115111 A1 May 9, 2013

(30) Foreign Application Priority Data
Nov. 3, 2011 (DE) .................... 10 2011 117 527

(51) Int. Cl.
*F04F 5/20* (2006.01)
*A61B 17/88* (2006.01)
*B01F 13/00* (2006.01)

(52) U.S. Cl.
CPC ............ *F04F 5/20* (2013.01); *A61B 17/8822* (2013.01); *A61B 17/8825* (2013.01); *A61B 17/8827* (2013.01); *B01F 13/0027* (2013.01); *A61B 2017/883* (2013.01); *B01F 2215/0029* (2013.01)

(58) Field of Classification Search
CPC ........ F04F 5/14; F04F 5/20; A61B 17/8822; A61B 17/8825; A61B 17/8827; A61B 2017/8838; B01F 13/0027; B01F 2215/0029
USPC ...... 417/151, 55, 198; 606/213, 214, 92–95; 227/176.1; 604/82, 191; 366/139; 222/389, 190, 145.5, 566, 327, 386
See application file for complete search history.

(56) References Cited

U.S. PATENT DOCUMENTS

| 4,073,602 A * | 2/1978 | Cagle | 417/185 |
| 4,315,600 A * | 2/1982 | Rhoades | A01C 23/042 |
| | | | 137/564.5 |

(Continued)

FOREIGN PATENT DOCUMENTS

| CH | DE 4416312 A1 * | 4/1995 | ............. B60P 7/065 |
| DE | 36 40 279 A1 | 6/1987 | |

(Continued)

OTHER PUBLICATIONS

13667144—FileCarburetorpng—Wikimedia Commons 2007.*

(Continued)

*Primary Examiner* — Devon Kramer
*Assistant Examiner* — Jon Hoffmann
(74) *Attorney, Agent, or Firm* — Panitch Schwarze Belisario & Nadel LLP (57) ABSTRACT

A device is provided for generating a vacuum for a vacuum cementing device, the device including a channel and a connector for a gas cartridge. The connector has an opener for opening the gas cartridge, and connects the gas cartridge to the channel in a pressure-tight manner, such that gas from the opened gas cartridge flows along the channel to the surroundings of the device. The channel includes at least one T-piece, provided as Venturi nozzle, having a vacuum connector for the vacuum cementing device, such that gas from the opened gas cartridge flowing through the channel generates a negative pressure at the vacuum connector. A method is also provided including steps of opening a gas cartridge, flowing gas from the gas cartridge through a Venturi nozzle, whereby by a negative pressure is generated, and applying the negative pressure to a vacuum cementing system.

31 Claims, 4 Drawing Sheets

(56) References Cited

U.S. PATENT DOCUMENTS

| | | | | |
|---|---|---|---|---|
| 4,381,668 | A | * | 5/1983 | Sato ................. G01F 1/684 73/202.5 |
| 4,758,096 | A | | 7/1988 | Gunnarsson |
| 4,787,751 | A | * | 11/1988 | Bakels .................... 366/110 |
| 4,901,923 | A | * | 2/1990 | McRoskey et al. ......... 239/123 |
| 4,966,601 | A | * | 10/1990 | Draenert .................... 606/92 |
| 5,291,916 | A | * | 3/1994 | Kloosterman ........ B60T 17/02 137/112 |
| 5,514,135 | A | * | 5/1996 | Earle ........................... 606/93 |
| 5,551,778 | A | | 9/1996 | Hauke et al. |
| 5,779,536 | A | * | 7/1998 | McCorkel et al. .......... 454/137 |
| 5,788,463 | A | * | 8/1998 | Chan ........................... 417/63 |
| 6,035,818 | A | * | 3/2000 | Sato .................. F01L 1/34406 123/90.17 |
| 6,041,977 | A | * | 3/2000 | Lisi ..................... A21C 15/005 222/179 |
| 6,117,150 | A | | 9/2000 | Pingleton et al. |
| 6,165,201 | A | | 12/2000 | Sawhney et al. |
| 7,661,604 | B1 | * | 2/2010 | MacLean-Blevins ......... 239/10 |
| 2001/0008968 | A1 | * | 7/2001 | Overes et al. ................ 606/93 |
| 2004/0112378 | A1 | * | 6/2004 | Djupesland ............ A61B 5/085 128/203.12 |
| 2005/0178854 | A1 | * | 8/2005 | Dodd .......................... 239/310 |
| 2007/0208337 | A1 | | 9/2007 | Podhajsky et al. |
| 2010/0059605 | A1 | * | 3/2010 | Plantz et al. ................ 239/316 |
| 2010/0076480 | A1 | * | 3/2010 | Lu et al. ..................... 606/192 |
| 2010/0091606 | A1 | | 4/2010 | Kwan et al. |
| 2010/0262152 | A1 | * | 10/2010 | Shadduck et al. ............ 606/94 |
| 2010/0329074 | A1 | | 12/2010 | Vogt et al. |
| 2011/0229346 | A1 | * | 9/2011 | Kim et al. .................... 417/171 |
| 2011/0272437 | A1 | | 11/2011 | Vogt et al. |
| 2012/0172789 | A1 | | 7/2012 | Fischer et al. |

FOREIGN PATENT DOCUMENTS

| | | | | |
|---|---|---|---|---|
| DE | 102010019224 | B3 | | 10/2011 |
| EP | 0 692 229 | A1 | | 1/1996 |
| EP | 1 005 901 | A2 | | 6/2000 |
| EP | 1 016 452 | A2 | | 7/2000 |
| EP | 1020167 | A2 | | 7/2000 |
| EP | 2269718 | A2 | | 1/2011 |
| FR | 1170550 | A | * | 1/1959 ............ A61M 39/02 |
| JP | 2001-509411 | A | | 7/2001 |
| JP | 2002-522177 | A | | 7/2002 |
| JP | 2007-236940 | A | | 9/2007 |
| WO | 94/26403 | A1 | | 11/1994 |
| WO | 99/67015 | A1 | | 12/1999 |
| WO | 0035506 | A1 | | 6/2000 |
| WO | 03009766 | A1 | | 2/2003 |
| WO | 2011029573 | A1 | | 3/2011 |

OTHER PUBLICATIONS

13667144-ProquestTranslation-FR1170550A.pdf.*
13667144-ProquestTranslation-DE4416312A1.pdf.*
Office Action issued Feb. 13, 2014 in CA Application No. 2,790,746.
European Search Report issued Mar. 12, 2013 in EP Application No. 12006613.9.
English translation of an Office Action issued May 30, 2014 in CN Application No. 201210432297.X.
Charnley, "Anchorage of the Femoral Head Prosthesis to the Shaft of the Femur", The Journal of Bone and Joint Surgery, vol. 42 B, No. 1, pp. 28-30 (1960).
English translation of an Office Action issued Dec. 24, 2013 in JP Application No. 2012-211394.
Office Action issued Jan. 3, 2014 in AU Application No. 2012227362.

* cited by examiner

DEVICE AND METHOD FOR GENERATING VACUUM FOR VACUUM CEMENTING SYSTEMS

BACKGROUND OF THE INVENTION

The invention relates to a device for generating a vacuum for a vacuum cementing device. The invention also relates to a method for generating a negative pressure in a vacuum cementing system.

Conventional PMMA bone cements have been known for decades and are based on the ground-breaking work of Sir Charnley (Charnley, J., "Anchorage of the Femoral Head Prosthesis of the Shaft of the Femur," *J. Bone Joint Surg.* 42: 28-30 (1960)). The basic structure of PMMA bone cements has remained the same ever since. PMMA bone cements consist of a liquid monomer component and a powder component. The monomer component generally contains the monomer, methylmethacrylate, and an activator (N,N-dimethyl-p-toluidine) dissolved therein. The powder component consists of one or more polymers made by polymerization, preferably suspension polymerization, based on methylmethacrylate and co-monomers, such as styrene, methylacrylate or similar monomers, a radio-opacifier, and the initiator, dibenzoylperoxide. Mixing the powder component and the monomer component, a dough that can be shaped plastically is generated by swelling of the polymers of the powder component in the methylmethacrylate. When the monomer component and the powder component are being mixed, the activator, N,N-dimethyl-p-toluidine, reacts with dibenzoylperoxide which disintegrates while forming radicals. The radicals thus formed trigger the radical polymerization of the methylmethacrylate. Upon advancing polymerization of the methylmethacrylate, the viscosity of the cement dough increases until the cement dough solidifies and thus is cured.

Polymethylmethacrylate bone cements can be mixed by mixing the cement powder and the monomer liquid in suitable mixing beakers with the aid of spatulas. This procedure is disadvantageous in that air inclusions may be present in the cement dough thus formed and cause destabilization of the bone cement later on. For this reason, it is preferred to mix bone cement powder and monomer liquid in vacuum mixing systems, since mixing in a vacuum removes air inclusions from the cement dough to a large extent and thus achieves optimal cement quality.

Bone cements mixed in a vacuum have clearly reduced porosity and thus show improved mechanical properties. A large number of vacuum cementing systems have been disclosed of which the following shall be listed for exemplary purposes: U.S. Pat. Nos. 5,624,184; 4,671,263; 4,973,168; 5,100,241; 5,586,821; and 5,344,232; International patent application publication Nos. WO99/67015 and WO94/26403; European patent application publications EP 1 020 167 A1; EP 1 016 452 A1; EP 0 692 229 A1; and EP 1 005 901 A1; and German published patent application DE 36 40 279 A1.

In the vacuum cementing systems that are currently common in the market, the requisite vacuum is generated by vacuum pumps driven by non-sterile compressed air. These hose systems are heavy and always associated with a risk of accidents since they are routed on the floor. Moreover, it is also feasible to provide vacuum in the operating theatre by central vacuum line systems. Since long hoses are used in this case, this also results in problems related to the risk of accidents and poor handling properties. Moreover, a vacuum needs to be generated at the site of the surgery or in its immediate vicinity, which means that a supply of compressed air and/or electrical power needs to be available. This is not always feasible if a surgery (operating room) is to be performed in less developed regions, at an accident site, in makeshift emergency operating theatres, in tents, or in a field hospital.

BRIEF SUMMARY OF THE INVENTION

It is an object of the invention to overcome the disadvantages of the prior art. In particular, a mobile and lightweight device for generating vacuum for cementing systems is to be provided. It would also be advantageous if the device did not require long and heavy hoses and did not need to be connected to stationary compressed air systems, a mains power system or vacuum systems. An easily handled, safe device is to be provided to a medical user in the operating theatre. One aim is to design the device to be so simple that it can be made of inexpensive materials and thus allow it to be manufactured economically as a dispensable article.

It is also an object of the invention to develop a method that is as simple as possible and can be used by the OR staff during an ongoing surgery with minimal time expenditure to produce a bone cement in a vacuum.

The objects of the invention are met and further problems not mentioned here are solved in that the device comprises a channel and a connector for a gas cartridge, wherein the connector comprises an opener for opening the gas cartridge, and the gas cartridge can be or is connected by the connector to the channel in a pressure-tight manner, such that a gas from the opened gas cartridge flows along the channel, wherein the channel connects the connector to the surroundings of the device and the channel comprises at least one T-piece having a vacuum connector for the vacuum cementing device, wherein the T-piece is provided as a Venturi nozzle, such that the gas from the opened gas cartridge flowing through the channel generates a negative pressure at the vacuum connector.

Based on these features, a device is provided that does not to have any cables and any other lines and is still capable of providing a vacuum, at least for short periods of time, for mixing a medical cement.

A vacuum shall be understood herein also to mean a gross vacuum, that means a minor negative pressure as well. Preferably, a vacuum or a negative pressure shall be understood to mean a gas pressure of less than or equal to 300 mbar, particularly preferably of less than or equal to 80 mbar.

A device according to the invention can provide at least one operable blocking element to be arranged in the channel, which makes the gas flow from the opened gas cartridge through the channel interruptible and/or adjustable, wherein, in particular, the operable blocking element comprises a restoring element which preferably comprises a spring element, particularly preferably a spring element made of metal.

A blocking element, for example a valve, allows the device to be controlled more easily and thus offers better ease of use. A vacuum can just as well be applied consecutively to multiple vacuum cementing systems using the device, provided the gas cartridge still contains sufficient compressed gas. In this context, the invention can provide the blocking element to be a valve or the blocking elements to be valves, preferably at least one rotary valve, one ball valve, one pinch valve, one pin valve and/or one slider.

Valves of this type are easy and inexpensive to assemble and thus are particularly well-suited for implementing an inexpensive device.

In this context, the invention can also provide the valve to be a conical, at least partially rotationally-symmetrical body, which is supported as in a bearing in a matching conical opening in the device such that it can be rotated, wherein the external walls of the valve are tight against the walls of the conical opening in the device, except for the openings of the channel, in each position of the valve such that the connections are tight, at least with respect to the channel.

A valve of this type can be pressed into the conical opening of the device, for example by a wedge, such that this very simple design achieves that the valve is situated in a press-fit. Valves of this type are easy to manufacture from plastic materials by injection molding techniques.

Another particularly preferred embodiment of the invention can provide that the connector comprises an internal thread for receiving a gas cartridge fitted with an external thread. A thread is a simple means that allows a large force to be exerted on a pre-determined breakage site on the gas cartridge. Moreover, many commercial gas cartridges are already provided with a thread of this type such that they can be used for a device according to the invention.

Moreover, the invention can provide that the connector comprises a seal, preferably a rubber gasket, for sealing the connection of the gas cartridge with respect to the channel. This allows prevention of a possible malfunction due to no gas or an insufficient amount of gas flowing into the channel. Moreover, the efficiency of the device is increased if the seal renders the connector tight up to the highest pressure possible.

According to another embodiment, the invention can provide that the opener comprises a mandrel, preferably a hollow mandrel, that forms one end of the channel. This is a simple and inexpensive option for implementing an opener. In particular, in combination with a thread on the gas cartridge and, optionally, a turning handle being attached to the gas cartridge, this allows the gas cartridge to be opened easily.

In this context, the invention can provide that the opener comprises an operable pressure-exerting facility whereby the gas cartridge can be pressed onto the mandrel, in particular in the area of a membrane serving as a pre-determined breakage site of the gas cartridge, whereby the gas cartridge can thus be opened and whereby the pressure-exerting facility preferably can be rotated.

Another particularly preferred embodiment of the invention can be implemented in that the device comprises a gas cartridge, wherein the gas cartridge is incorporated in the device in the area of the opener in such a manner that it can be opened by operating the opener, wherein the gas cartridge preferably comprises an external thread that engages the internal thread of the connector. The gas cartridge being incorporated already simplifies its application, which is a major advantage in the often very busy OR operation.

Particularly preferred embodiments of the invention result from providing that the Venturi nozzle is formed by a tapering of the channel, and that the vacuum connector is connected to the channel in the area of the tapering, wherein a Laval nozzle is preferably formed. The tapering provides for acceleration of the gases flowing through it and thus provides for a lower gas pressure perpendicular to it, which means a better vacuum at the vacuum connector.

The invention can just as well provide that the device comprises at least one actuator, which can be used to operate the opener and/or the blocking element, wherein the actuator is provided as a trigger, button or pedal, and wherein the actuator preferably comprises a restoring element, in particular having a metal spring. The operating facilities are particularly well-suited for OR operation since they necessitate no laborious measures for operating the device.

The invention can just as well provide a handle for holding the device to be arranged on the underside of the device, wherein the actuator preferably is a trigger or a button in the area of the handle of the device such that the device can be operated by one hand. This allows the device to be held in the hand to simplify manual operation of the device.

Alternatively, the invention can provide the device to be provided with a level floor for set-up on a level underground, wherein the actuator preferably is a pedal or a button on the upper side of the device. This variant enables the device to be placed down on the floor of an operating theatre. The user's hands are then unoccupied and available to perform other activities.

It is particularly preferable for the invention to provide the device to consist essentially of plastic material, preferably to consist of plastic material with the exception of the opener, gas cartridge and/or restoring element, non-return valve or restoring elements.

The use of plastic materials ensures that the manufacturing costs of the device are low. Moreover, some plastic materials are particularly well-suited for medical devices. Accordingly, manufacturing from inexpensive plastic injection molded parts, which can be assembled with little assembly effort, is particularly preferred as well.

Moreover, the invention can provide the mass of the device to be less than 10 kg, preferably between 0.1 kg and 5 kg, particularly preferably between 0.5 kg and 3 kg. The mass of the device being low simplifies the handling of the device.

According to another particularly preferred embodiment, the invention can provide the cross-sectional area of the channel at its thinnest place to be less than 10 mm$^2$, in particular to be between 0.1 mm$^2$ and 5 mm$^2$ and/or the channel to form a narrow gap having a width of less than 1 mm or to be a slender tube having a diameter of less than 1 mm. The cross-sectional areas, widths, and diameters of the channel as specified ensure that gas from common gas cartridges flows through the device for a sufficiently long period of time, i.e. the negative pressure or the vacuum is maintained for a sufficiently long time, to allow a medical cement to be mixed.

The invention can also provide the geometry and the flow resistance of the channel to be matched to the capacity of the gas cartridge, in such a manner that the gas from the opened gas cartridge can flow for at least 5 sec. from the gas cartridge through the channel before the gas cartridge no longer contains any compressed gas, preferably between 10 sec. and 100 sec., more preferably between 20 sec. and 60 sec., and particularly preferably between 25 sec. and 45 sec. The periods of time are particularly well-suited for mixing of a medical cement.

Another embodiment of the device according to the invention can provide a non-return valve to be arranged in the vacuum connector, wherein the non-return valve can be opened by the negative pressure generated by the Venturi nozzle and then closes the vacuum connector when no or only very little gas flows from the opened gas cartridge through the channel, and wherein the non-return valve preferably comprises a restoring element. This measure is particularly well-suited for dispensing with a blocking facility. Moreover, the device is thus sealed and is therefore less susceptible to disturbance. Mainly, however, the vacuum in the connected vacuum cementing system can thus be maintained, even if the device is not operated again.

Particularly preferably, the invention can provide the Venturi nozzle to merge into an outflow channel having a larger diameter that is connected to the surroundings of the device in a gas-permeable manner, wherein the outflow channel preferably has a silencer arranged in it, particularly preferably in the region of the merging site to the surroundings of the device. This improves the flow velocity of the gas and therefore the vacuum that is being generated. The purpose of the silencer is to prevent disturbing noise generated by the flowing gas.

The invention can also provide that the device is or can be connected by the vacuum connector to a vacuum cementing system for producing a medical bone cement.

The object of the invention is also met by a method for generating a negative pressure in a vacuum cementing system, in particular having a device of this type, comprising the following steps:

opening a gas cartridge;
flowing the gas from the gas cartridge through a Venturi nozzle such that a negative pressure is generated; and
applying the negative pressure to the vacuum cementing system.

In this context, the invention can provide the blocking element to be opened after the gas cartridge is opened, and the gas to flow through the Venturi nozzle after the blocking element is opened. This allows for better control over the method.

The invention can just as well provide a medical cement, in particular a medical bone cement, to be mixed under the action of the negative pressure in the vacuum cementing system.

The invention is based on the surprising finding that a simple device, which is independent of external supply and utilizes a compressed gas, can be used to generate a vacuum for mixing a medical cement. The invention makes use of a compressed gas flowing out and generates a negative pressure by providing a Venturi nozzle to be situated in the flow path. Since the gas flow is switchable, the use of an actuator allowing a blocking facility or an opener for a gas cartridge to be operated allows the negative pressure to be switched as well. The measures according to the invention allow a negative pressure, which is sufficient for mixing a medical cement, to be provided for a short period of time. The short period of time is sufficiently long to allow the medical cement to be mixed under the effect of the negative pressure.

Therefore, the device according to the invention can be operated even in the absence of electrical motors and thus in the absence of electrical power or potentially environmentally-hazardous batteries and rechargeable batteries. Its use is feasible without any problem, even under difficult conditions with no access to further resources.

An exemplary device according to the invention for generating a vacuum comprises:

a) a pressure body;
b) a cylindrical opening in the pressure body, the opening having an internal thread for receiving a gas cartridge having an external thread;
c) a seal on the bottom of the cylindrical opening;
d) a hollow mandrel arranged below the seal on the bottom of the cylindrical opening and projecting outward through an opening of the sealing disc;
e) a gas cartridge filled with compressed gas, the gas cartridge being screwed into the internal thread of the cylindrical opening by its external thread;
f) an opener that can be rotated about its axis and that is connected to the gas cartridge in a non-rotatable manner, for rotating the gas cartridge;
g) an opening in the pressure body for receiving a switchable blocking element, wherein the opening is connected in a gas-permeable manner by a channel to the cylindrical opening having an internal thread;
h) a channel connecting the opening to a nozzle in a gas-permeable manner, wherein the nozzle merges into an outflow channel connected by a channel to the outside of the pressure body in a gas-permeable manner;
i) a switchable blocking element that can connect or separate the channel in a gas-permeable manner or in a gas-impermeable manner, respectively, and that is arranged in the opening, wherein the switchable blocking element is connected to a restoring element; and
j) an outflow channel connected to the channel and into which merges the nozzle, wherein the outflow channel preferably is provided as a Laval nozzle, the opening of the nozzle is oriented in the direction of the conical tapering of the Laval nozzle, and the outflow channel is connected to the surrounding atmosphere in a gas-permeable manner.

An alternative device according to the invention can comprise:

a) a pressure body;
b) a cylindrical opening in the pressure body, the cylindrical opening having an internal thread for receiving a gas cartridge having an external thread;
c) a seal on the bottom of the cylindrical opening;
d) a hollow mandrel arranged below the seal on the bottom of the cylindrical opening and projecting outward through an opening of the sealing disc;
e) a gas cartridge screwed into the internal thread of the cylindrical opening by its external thread;
f) an opener that can be rotated about its axis and that is connected to the gas cartridge in a non-rotatable manner, for rotating the gas cartridge;
g) an opening in the pressure body for receiving a switchable rotary valve, wherein the opening is connected in a gas-permeable manner by a channel to the cylindrical opening having an internal thread;
h) a second channel connecting the opening to a nozzle in a gas-permeable manner, wherein the nozzle merges into an outflow channel connected in a gas-permeable manner by a third channel to the outside of the pressure body;
i) a rotary valve that can connect the first channel to the second channel in position in a gas-permeable manner or separate them in gas-impermeable manner and that is arranged in the opening, wherein the rotary valve is connected to a restoring element; and
j) an outflow channel connected to the second channel and having the nozzle merge into it, wherein the outflow channel is provided as a Laval nozzle, the opening of the nozzle is oriented in the direction of the conical tapering of the Laval nozzle, and the outflow channel is connected to the surrounding atmosphere in a gas-permeable manner.

The pressure bodies form a pressure-resistant housing for the device.

It is particularly advantageous to use gas cartridges containing liquefied gas, such as liquid carbon dioxide, in the device. In addition, all other non-toxic gases are expedient as well.

Optionally, the outflow channel can also contain a silencing element, such as porous discs, felt discs or woven cloth discs, in order to silence the noise of the gas flowing out.

The blocking element can be provided as a rotary valve, ball valve, pinch valve, pin valve, and/or slider, with a rotary valve being particularly preferred. The blocking element can be connected in a non-positive (force-fit) or positive (form-fit) manner to an actuator, such as a trigger or a foot button or a push-button. This enables manual actuation or foot actuation of the blocking element.

The restoring element can be provided as a coil spring or a leaf spring and preferably comprises spring steel. The gas cartridge is also made from metal and preferably comprises steel or an aluminum alloy.

The device according to the invention can be arranged in a housing. In this context, the actuator can be provided as foot button or as trigger and project from the housing or be arranged in a recess in the housing, in such manner that manual actuation or foot actuation of the actuator is made feasible.

The device can be provided to the medical user in non-sterile or in sterile condition. It is advantageous that the device with the gas contained in the gas cartridge can be sterilized by gamma sterilization. This also allows the sterile gas to be released into the atmosphere of the operating theatre without any problem and without causing microbial contamination.

The device according to the invention also includes a method for generating vacuum using the device. The method according to the invention can be characterized by the following consecutive steps:
  a) rotating the opener until the gas cartridge is moved against the mandrel, such that a membrane of the gas cartridge is perforated;
  b) flowing the compressed gas out up to the blocking element;
  c) opening the blocking element by actuation of the foot button or trigger, such that the compressed gas flows through the channel to the nozzle, expands while flowing through the nozzle into the outflow channel, and then is released through the outflow channel to the surrounding atmosphere;
  d) wherein a negative pressure is established on or about the nozzle and the negative pressure expands to the vacuum connector.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
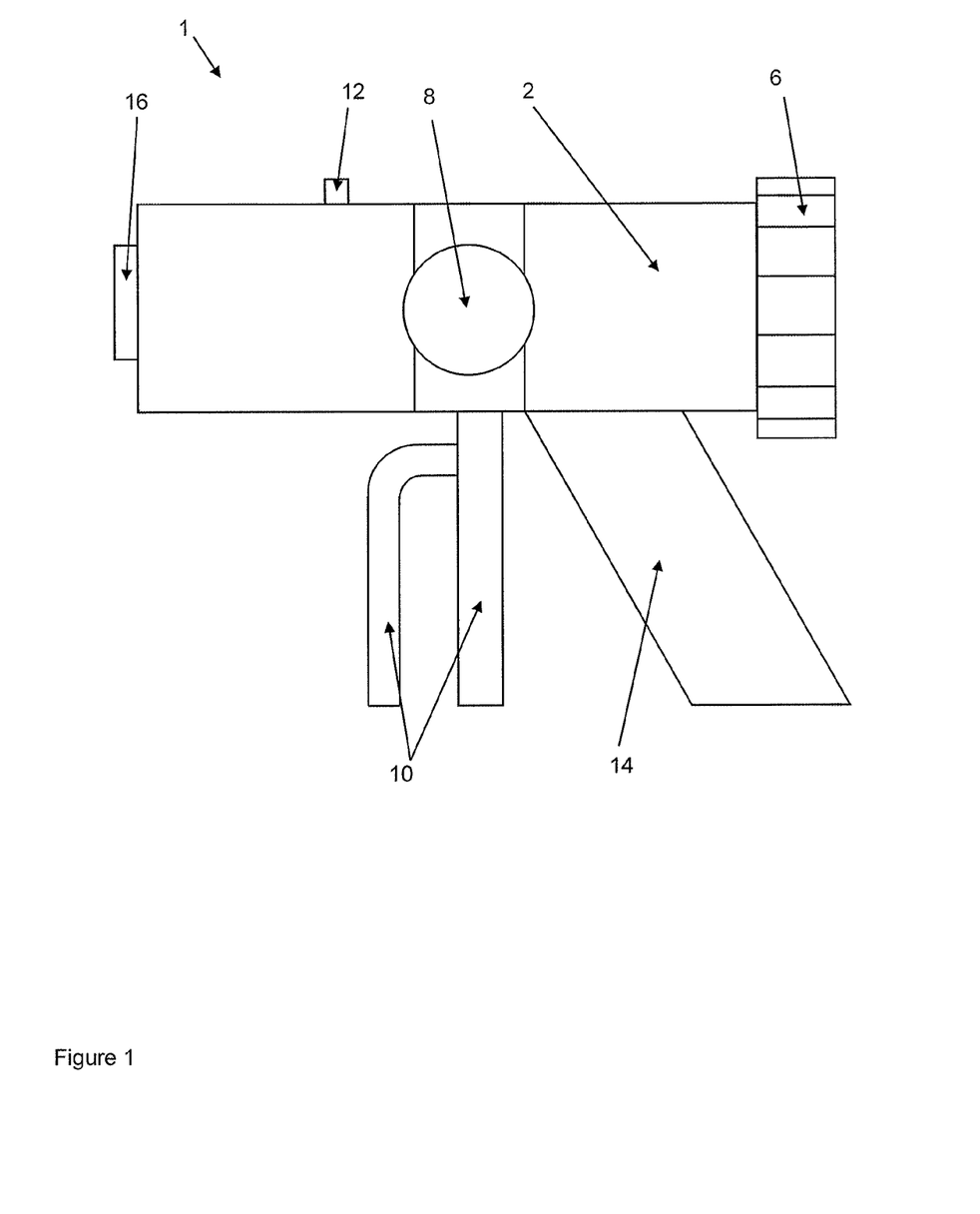
FIG. 1 is a schematic side view of a device having a handle according to an embodiment of the invention for generating a vacuum for a vacuum cementing device.

FIG. 1 shows a schematic cross-sectional view of a device 1 according to an embodiment of the invention for generating a vacuum for a vacuum cementing device. The device 1 comprises a housing 2 having a gas cartridge (not shown) arranged in it. The rear side of the device 1 is closed by a screw lid 6, such that the gas cartridge can be shifted on the inside of the device and pressed onto a mandrel or blade that opens the gas cartridge.

A rotatable valve 8 is arranged in the middle of the device 1 and can be used to open and close a channel (not shown) arranged on the inside of the device 1. The rotatable valve 8 is conical in shape and comprises a bushing that can connect a front part and a rear part of the channel in suitable position of the valve 8 and thus opens the channel. The rotatable valve 8 is shaped slightly conical and is seated in a press-fit in an opening of the housing 2 in the device 1, such that a gas-tight connection of the bushing to the channel or gas-tight closure of the channel is made feasible.

The rotatable valve 8 can be operated by a trigger 10. The rotatable valve 8 can be connected to an elastic restoring element, that causes the valve to be situated in a closed position when no force acts on the trigger 10. A vacuum connector 12 is arranged on the upper side of the device 1 and comprises, on the inside of the device 1, a feed line that reaches the channel and is perpendicular to the channel, wherein the connection of the feed line to the channel forms a Venturi nozzle, such that a flow through the channel generates a negative pressure at the vacuum connector 12. A vacuum cementing device (not shown) can be or is connected to the vacuum connector 12.

A handle 14 is arranged on the underside of the device 1, such that the device can be held in the manner of a pistol, and the trigger 10 can be operated with the same hand holding the device 1 by its handle 14. The channel in device 1 merges on the front into a gas outlet 16, such that the gas from the gas cartridge can flow to exit the device when the valve 8 is open.

Figure 2:
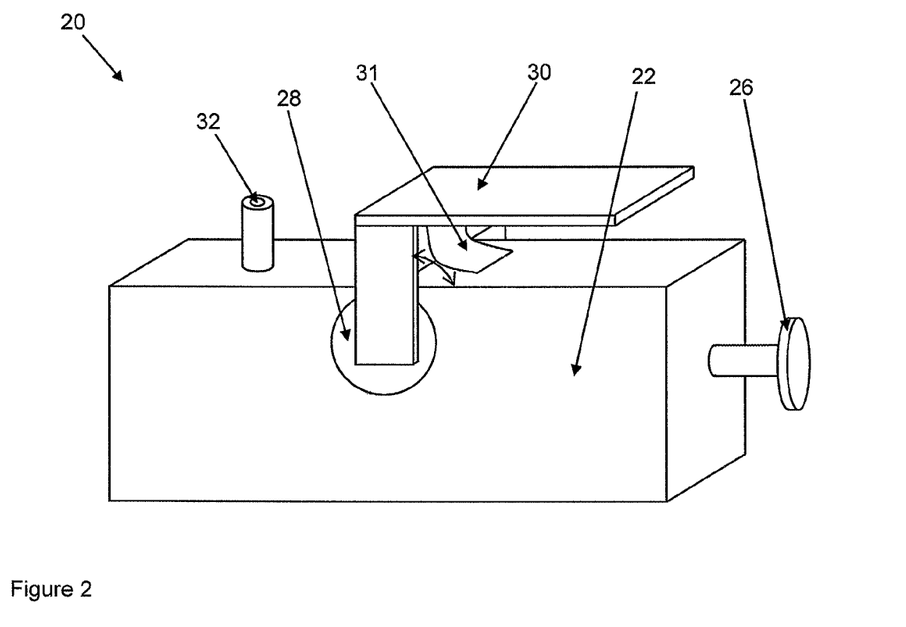
FIG. 2 is a schematic perspective view of an alternative device for set-up on the floor according to the invention for generating a vacuum for a vacuum cementing device.
Figure 3:
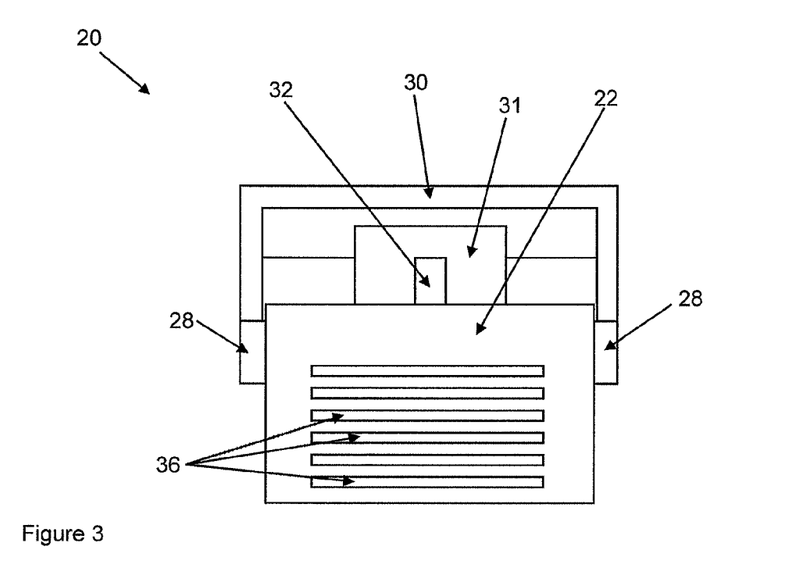
FIG. 3 is a schematic front view of the device according to FIG. 2.

FIGS. 2 and 3 show an alternative device 20 according to the invention for generating a vacuum for a vacuum cementing device that can be operated by foot and can be placed on the floor of an OR theatre. FIG. 2 shows a schematic perspective view of the device and FIG. 3 shows a schematic front view of the device. The inside of a housing 22 of the device 20 has a channel having a Venturi nozzle (not shown) and a compressed gas cartridge (not shown) arranged in it, analogous to the embodiment according to FIG. 1.

A rotary handle 26 is arranged on the rear end of the device 20 and can be rotated into the device 20 and thus opens the compressed gas cartridge on the inside of the device 20.

A rotatable valve 28 extends through the device 20 and can either close or open the channel on the inside of the device 20 depending on its position. The valve can be operated by a foot button 30 on the upper side of the device 20. A leaf spring serving as restoring spring 31 for the foot button is arranged on the underside of the foot button 30. Accordingly, a pedal is thus formed on the upper side of the device 20 that can be used to operate the valve 28, whereby the channel can be opened and closed by foot. The effect of restoring spring 31 is that the foot button 30 remains in the position shown, provided the foot button 30 is not being pressed down. The valve 28 is opened when it is situated in its pressed-down position (not shown), and the valve 28 is closed in the unloaded position shown.

A vacuum connector 32 in the form of a tube is arranged on the upper side of the device 20. The vacuum connector 32 can comprise a common quick-plug connection for vacuum connectors. A vacuum cementing device (not shown) can be connected by the vacuum connector 32. The front of the device 20 has slits of a gas outlet 36 arranged in it, into which the channel merges and through which the gas can flow to exit the channel and into the surroundings.

The first step of the operation of device 20 is to operate the rotary handle 26. This opens the compressed gas cartridge that is arranged on the inside of the device 20. Instead of the rotary handle 26, a push-button could just as well be arranged in the same place to open the compressed gas cartridge upon being operated. Accordingly, the compressed gas cartridge could just as well be opened by foot, for example with a slight kick. The push-button could just as well be operated by a pedal or even by the foot button 30.

Once the gas cartridge has been opened, the gas flows from the cartridge into the channel, but is stopped by the closed valve 28. Operating the valve 28 by the foot button 30 allows the valve 28 to be opened and thus a flow through the channel can be generated. Having a Venturi nozzle on the inside of the device 20 thus generates a vacuum, or a negative pressure, at the vacuum connector 32. The vacuum may be applied to a vacuum cementing device, such that a medical cement can be mixed therein in a vacuum.

Figure 4:
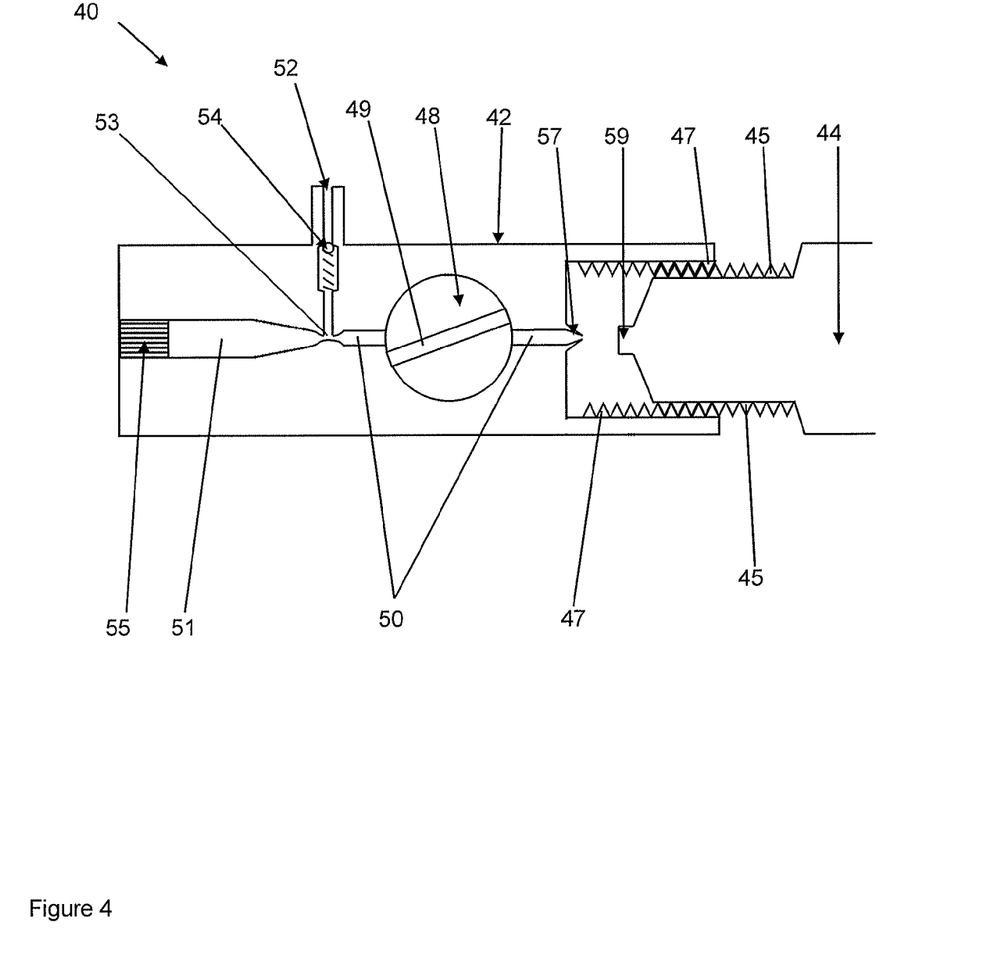
FIG. 4 is a schematic cross-sectional view of a third device according to the invention for generating a vacuum for a vacuum cementing device.

FIG. 4 shows a schematic cross-sectional view of a device 40 according to the invention for generating a vacuum for a vacuum or a negative pressure. The vacuum or negative pressure is applied to the vacuum cementing system in order to mix a medical cement, in particular a bone cement, at a negative pressure or in a vacuum.

The device 40 is made from plastic material using an injection molding procedure. The central part is a housing 42 which is provided to be largely solid. A gas cartridge 44 filled with a gas under the effect of a pressure is arranged in the rear part of the device (on the right in FIG. 4). The gas cartridge 44 can just as well be filled with a liquefied gas that transitions to the gaseous state at normal pressure. The gas cartridge 44 comprises an external thread 45 that can engage an internal thread 47 in the device 40. The internal thread 47 is arranged in an opening in the rear part of the device 40, which is designed to have the gas cartridge 44 inserted into it.

A valve 48 is arranged in a rotatable and press-fit manner in a recess of device 40 designed for this purpose. A bushing 49 in the form of a cylindrical tube is arranged in the rotatable valve 48. The bushing 49 is well-suited for opening or closing a channel 50 on the inside of the device 40 depending on the position of the valve 48. FIG. 4 shows the closed position of the valve 48. The channel 50 is provided in the front part of the device 40 (on the left in FIG. 4) in the form of outflow channel 51 which has a larger diameter. The channel 50 and the outflow channel 51 are cylindrical tubes of variable diameters or gaps of variable width.

A vacuum connector 52 is arranged on the upper side of the device 40 and can be or is connected to a vacuum cementing system (not shown). A feed line of the vacuum connector 52 reaches the channel 50 at a narrowing of the channel 50 and is connected to it in this place. The channel 50 and the feed line of the vacuum connector 52 form a T-piece 53 in this place. In this context, the channel 50 forms a linear bushing which the feed line reaches in perpendicular orientation. By the narrowing of the channel 50, the T-piece 53 forms an efficient Venturi nozzle 53. If the geometry of the channel 50 in the area of the T-piece 53 is appropriate, the Venturi nozzle 53 can just as well be provided as a Laval nozzle.

The feed line to the vacuum connector 52 has a non-return valve 54 arranged in it which is implemented by a ball and a spring in an expanded area of the feed line to the vacuum connector 52. The ball, coming from the expanded area, can close the opening and is held in this position by the spring. As soon as the Venturi nozzle 53 generates a negative pressure, the non-return valve 54 is pulled downwards and the negative pressure is applied to the vacuum connector 52. The purpose of the non-return valve 54 is to seal the device 40, such that the same could be operated just as well without the valve 48. In this case, it is only necessary to open the gas cartridge 44 in order to generate the negative pressure at the vacuum connector 52. Moreover, the non-return valve 54 causes the vacuum in the vacuum cementing system to be maintained even if no gas flows through the channel 50 any longer. As soon as the compressed gas cartridge 44 is empty, no negative pressure is applied any longer and the device 40 is spent or needs to be re-loaded using a new compressed gas cartridge 44.

If the device 40 comprises a valve 54, it is feasible to dispense with a non-return valve 54 as a matter of principle.

The merging site of the outflow channel 51 to the surroundings of the device 40 has a silencer 55 arranged in it, which is intended to silence the sound waves generated while the gas flows through channel 50, 51. Accordingly, the purpose of the silencer 55 is just to provide a less noisy device 40, but the silencer 55 is not significant for the basic principle of the device 40. At the rear end of the device 40, the channel 50 merges into a hollow mandrel 57, which is designed for puncturing a designated site, in particular a membrane at the head 59 the gas cartridge 44.

Accordingly, when the gas cartridge 44 is screwed into the opening at the rear end of the device 40, the hollow mandrel 57 opens the gas cartridge 44. The gas flows through the hollow mandrel 57 into the channel 50. In order for the compressed gas from the gas cartridge 44 to not exit past the hollow mandrel 57, it is preferred to provide a gasket at the connector for the gas cartridge 44.

Initially, the valve 48 is in its closed state. The valve 48 is rotated by an actuator (not shown) such as a lever, a switch, a button, a foot button or a trigger, and the bushing 49 is thus rotated into the channel 50. This renders the valve 48 open, and the channel 50 including the bushing 49 extends from the gas cartridge 44 to the merging site of the outflow channel 51 out of the device 40.

Accordingly, the gas from the gas cartridge 44 can then flow through the entire channel 50. The flow velocity of the gas is increased in the area of the Venturi nozzle 53. In line with the laws of Bernoulli, this causes a negative pressure to be generated in the feed line of the vacuum connector 52, which reaches the channel 50 in perpendicular orientation. The non-return valve 54 in the feed line opens, and the negative pressure is thus applied to the vacuum connector 52. The negative pressure is passed through a line into the vacuum cementing system, such that a cement can be mixed therein at a negative pressure. In this context, the gas flows with little noise out of the device 40 through the silencer 55 to the surroundings. When the gas ceases to flow from the gas cartridge 44, the non-return valve 54 closes such that the mixing in the vacuum cementing system at a negative pressure or in a vacuum can continue to proceed.

Figure 5:
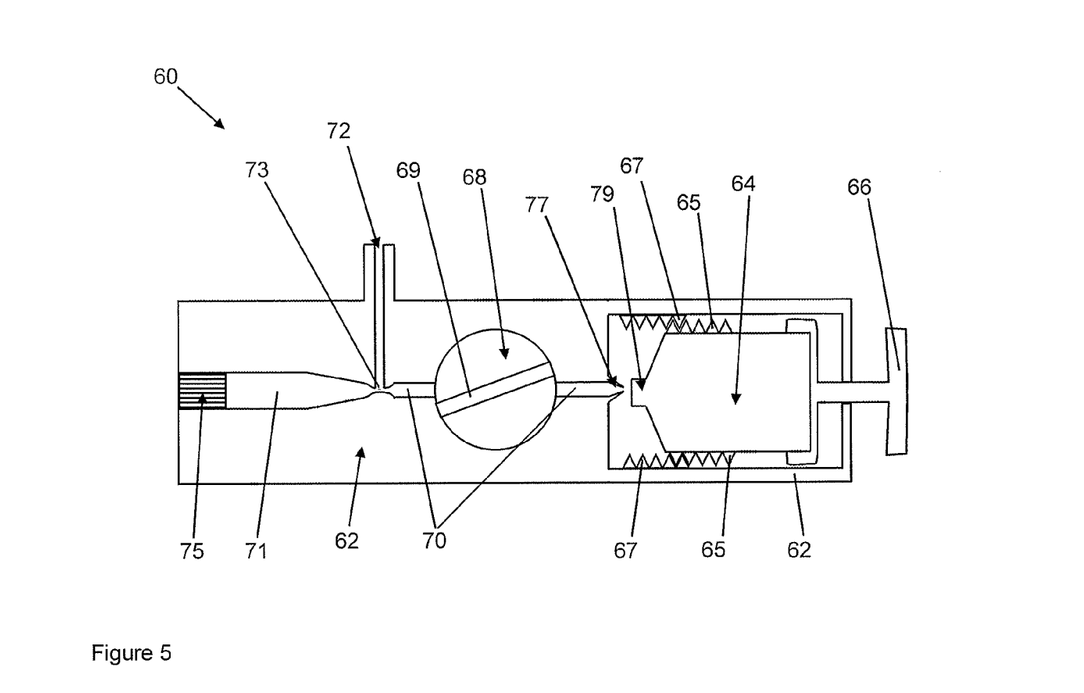
FIG. 5 is a schematic cross-sectional view of a fourth device according to the invention for generating a vacuum for a vacuum cementing device.

FIG. 5 shows another schematic cross-sectional view of another device 60 according to the invention with a similar structure to the device 40 according to FIG. 4. A gas cartridge 64 that is supported in the device 60, so as to be mobile in longitudinal direction (from right to left in FIG. 5), is arranged in a housing 62. The gas cartridge 64 is arranged in a hollow space in the rear end of the device 60. The hollow space has an internal thread 67 provided in it, which engages an external thread 65 of the gas cartridge 64. The gas cartridge 64 has a rotary handle 66 attached to it, which can be used to rotate the gas cartridge 64 into the external thread 67 and thus to shift it in longitudinal direction.

A valve 68, supported such as to be rotatable and having a bushing 69, is arranged on the inside of the device 60. In the closed position of the valve 68 as shown, the valve seals a channel 70 that extends from the hollow space at the rear end of the device 60 to an outlet at the front end of the device 60. The channel 70 is widened in the front area of the device and forms an outlet channel 71 having a larger diameter in this place. The valve 68 can be rotated to provide a through connection via the channels 70, 71 and the bushing 69, and to open the valve 68.

A vacuum connector 72 comprising a feed line is arranged on the upper side of the device 60. The feed line is connected to the channel 70 by a T-piece 73. In the area of the T-piece 73, the channel 70 has a smaller diameter than elsewhere in the device 60. An efficient Venturi nozzle 73 is thereby formed, such that a gas flowing through the channel 70 and the bushing 69 generates a negative pressure or a vacuum at the vacuum connector 72. A vacuum cementing system for mixing a medical cement can be or is arranged on the vacuum connector 72.

A silencer 75 is arranged in the outflow channel 71 in the area of the opening and is designed to silence noises caused by the flowing gas. The other end of the channel 70 has a hollow mandrel 77 arranged on it, which punctures and thus opens the gas cartridge 64 at its head 79, when the gas cartridge is screwed onto the hollow mandrel 77 by its rotary handle 66. The bushing of the rod of the rotary handle 66 to the hollow space for the gas cartridge 64 can be sealed by a gasket. In order to seal the connection from the gas cartridge 64 via the hollow mandrel 77 into the channel 70, a gasket can be arranged about the hollow mandrel 77 on the surface of the hollow space from which the hollow mandrel 77 projects.

The device 60 can be used in the same manner as the device 40 according to FIG. 4, wherein the device 60 comprises no non-return valve in the feed line of the vacuum connector 72, so that it is not possible to open a non-return valve. Like the valve 48 according to FIG. 4, the valve 68 can be operable by a button, a lever, a trigger or any other actuator, and can be rotated. The negative pressure is maintained here only for as long as gas still flows from the gas cartridge 64 and for as along as the valve 68 is in its open position.

The devices 40 and 60 can be operable both by hand and by foot. For this purpose, they can be designed to be held in the hand or to be placed on the floor.

Figure 6:
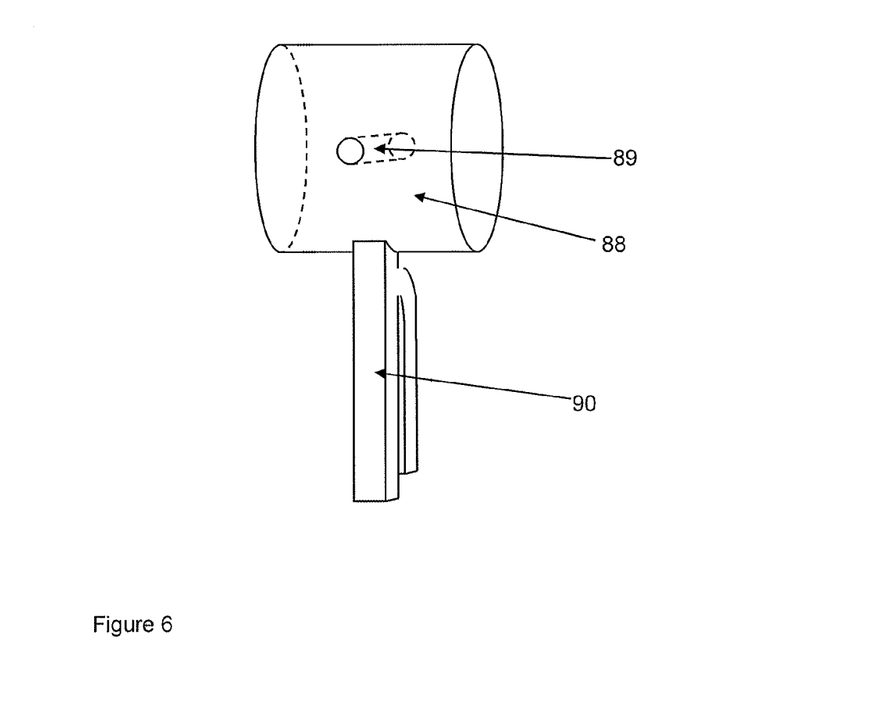
FIG. 6 is a schematic perspective view of a blocking element for a device according to an embodiment of the invention.

FIG. 6 shows a schematic perspective view of a rotary valve 88 having a bushing 89 and a trigger 90, which can be used, for example, in a device 1 according to the invention according to the embodiment of FIG. 1. Basically, a rotary valve 88 of this type can just as well be used in the devices 40, 60 according to the invention according to the embodiments of FIGS. 4 and 5, respectively.

The features of the invention disclosed in the preceding description and in the claims, figures, and exemplary embodiments, can be essential for the implementation of the various embodiments of the invention both alone and in any combination.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A device for generating a vacuum for a vacuum cementing device, the device comprising a channel and a connector for a gas cartridge, the connector comprising an opener for opening the gas cartridge, wherein the gas cartridge is connectable by the connector to the channel in a pressure-tight manner, such that a gas from the opened gas cartridge flows along the channel, wherein the channel connects the connector to surroundings of the device, wherein the channel comprises at least one T-piece forming a Venturi nozzle defined by a tapered portion of the channel and a vacuum connector extending transversely directly from the tapered portion for connecting to the vacuum cementing device, such that the gas from the opened gas cartridge flowing through the channel generates a negative pressure at the vacuum connector, the vacuum connector including a non-return valve therein, the non-return valve being opened when the negative pressure is generated.

2. The device according to claim 1, further comprising at least one operable blocking element arranged in the channel, the at least one operable blocking element operating to at least one of interrupt and adjust the gas flow from the opened gas cartridge, wherein the at least one operable blocking element comprises a restoring element.

3. The device according to claim 2, wherein the at least one operable blocking element comprises a spring element made of metal.

4. The device according to claim 2, wherein the at least one operable blocking element comprises at least one valve selected from a rotary valve, ball valve, pinch valve, pin valve, or a slider.

5. The device according to claim 4, wherein the at least one valve is supported in a bearing in a matching opening in the device, such that it is rotatable, and wherein external walls of the valve are tight against walls of the opening in the device, except for openings of the channel, in each position of the valve, such that connections are tight at least with respect to the channel.

6. The device according to claim 1, wherein the connector comprises an internal thread for receiving the gas cartridge fitted with an external thread.

7. The device according to claim 1, wherein the connector comprises a seal for sealing a connection of the gas cartridge with respect to the channel.

8. The device according to claim 7, wherein the seal comprises a rubber gasket.

9. The device according to claim 1, wherein the opener comprises a mandrel that forms one end of the channel.

10. The device according to claim 9, wherein the mandrel is a hollow mandrel.

11. The device according to claim 9, wherein the opener comprises an operable pressure-exerting facility, such that the gas cartridge is pressable onto the mandrel in a region of a membrane serving as a pre-determined breakage site of the gas cartridge, such that the gas cartridge is openable, and wherein the pressure-exerting facility is rotatable.

12. The device according to claim 1, further comprising the gas cartridge, the gas cartridge being incorporated in the device in a region of the opener, such that the gas cartridge is openable by operating the opener.

13. The device according to claim 12, wherein the gas cartridge comprises an external thread that engages an internal thread of the device.

14. The device according to claim 1, wherein the tapered portion forms a Laval nozzle.

15. The device according to claim 1, further comprising at least one actuator to operate at least one of the opener and a blocking element, wherein the at least one actuator is selected from a trigger, a button and a pedal, and wherein the actuator comprises a restoring element having a metal spring.

16. The device according to claim 15, further comprising a handle for holding the device, the handle being arranged on an underside of the device, wherein the actuator is selected from a trigger and a button located proximate the handle.

17. The device according to claim 1, wherein the device is provided with a level floor for set-up on a level base, and at least one actuator selected from a pedal and a button located on an upper side of the device, to operate at least one of the opener and a blocking element.

18. The device according to claim 1, wherein the device consists essentially of plastic material.

19. The device according to claim 1, wherein the device has a mass between 0.1 kg and 10 kg.

20. The device according to claim 19, wherein the device has a mass between 0.1 kg and 5 kg.

21. The device according to claim 1, wherein the channel has at least one of a cross-sectional area at its thinnest place of between 0.1 $mm^2$ and 10 $mm^2$ and the channel forms a narrow gap having a width or is a slender tube having a diameter.

22. The device according to claim 21, wherein the channel has a cross-sectional area at its thinnest place of between 0.1 $mm^2$ and 5 $mm^2$.

23. The device according to claim 1, wherein the channel has a geometry and flow resistance matched to a capacity of the gas cartridge in such manner that gas from the opened gas cartridge is flowable for at least 5 seconds from the gas cartridge through the channel before the gas cartridge no longer contains any compressed gas.

24. The device according to claim 23, wherein the gas from the opened gas cartridge is flowable for between 10 seconds and 100 seconds.

25. The device according to claim 1, wherein the non-return valve closes the vacuum connector when no or only very little gas flows from the opened gas cartridge through the channel, and wherein the non-return valve comprises a restoring element.

26. The device according to claim 25, wherein the device consists of plastic material except for at least one of the opener, the non-return valve, and the restoring element.

27. The device according to claim 1, wherein the Venturi nozzle merges into an outflow channel having a larger diameter connected to the surroundings of the device in a gas-permeable manner, and wherein the outflow channel has a silencer arranged therein in a region of the merging to the surroundings of the device.

28. The device according to claim 1, wherein the device is connectable by the vacuum connector to the vacuum cementing system for producing a medical bone cement.

29. A method for generating a negative pressure in a vacuum cementing system with a device comprising a channel and a connector for a gas cartridge, the connector comprising an opener for opening the gas cartridge, wherein the gas cartridge is connectable by the connector to the channel in a pressure-tight manner, such that a gas from the opened gas cartridge flows along the channel, wherein the channel connects the connector to surroundings of the device, wherein the channel comprises at least one T-piece forming a Venturi nozzle defined by a tapered portion of the channel and a vacuum connector extending transversely directly from the tapered portion for connecting to the vacuum cementing device, the vacuum connector including a non-return valve therein, the non-return valve being opened when negative pressure is generated, the method comprising:
 opening the gas cartridge;
 flowing gas from the gas cartridge through the Venturi nozzle such that the negative pressure is generated; and
 applying the negative pressure to the vacuum cementing system.

30. The method according to claim 29, further comprising opening a blocking element after the gas cartridge is opened, and flowing the gas through the Venturi nozzle after the blocking element is opened.

31. The method according to claim 29, further comprising mixing a medical bone cement under action of the negative pressure in the vacuum cementing system.

* * * * *